(12) United States Patent
Kim et al.

(10) Patent No.: US 10,781,148 B2
(45) Date of Patent: *Sep. 22, 2020

(54) METHOD OF PREPARING BUTADIENE

(71) Applicant: LG CHEM, LTD., Seoul (KR)

(72) Inventors: Mi Kyung Kim, Daejeon (KR); Jae Ik Lee, Daejeon (KR); Eun Kyo Kim, Daejeon (KR); Jeong Seok Lee, Daejeon (KR); Young Chang Byun, Daejeon (KR); A Ra Cho, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/098,053

(22) PCT Filed: Dec. 18, 2017

(86) PCT No.: PCT/KR2017/014966
§ 371 (c)(1),
(2) Date: Oct. 31, 2018

(87) PCT Pub. No.: WO2018/124580
PCT Pub. Date: Jul. 5, 2018

(65) Prior Publication Data
US 2019/0144361 A1    May 16, 2019

(30) Foreign Application Priority Data
Dec. 29, 2016    (KR) .................. 10-2016-0182471

(51) Int. Cl.
*C07C 5/48*    (2006.01)
*B01D 3/40*    (2006.01)
(Continued)

(52) U.S. Cl.
CPC .................. *C07C 5/48* (2013.01); *B01D 3/40* (2013.01); *B01D 5/003* (2013.01); *B01D 5/0003* (2013.01);
(Continued)

(58) Field of Classification Search
None
See application file for complete search history.

(56) References Cited

U.S. PATENT DOCUMENTS 3,383,429 A * 5/1968 Noddings .................. C07C 5/56
585/442
3,867,471 A * 2/1975 Aliev .................... C07C 5/3332
585/628
(Continued)

FOREIGN PATENT DOCUMENTS

JP    S59-167525    9/1984
JP    2016503820    2/2016
(Continued)

*Primary Examiner* — Tam M Nguyen
(74) *Attorney, Agent, or Firm* — Dentons US LLP

(57) ABSTRACT

A method of preparing butadiene and a device for preparing the same. The method includes passing reaction raw materials containing butene, oxygen, steam, and a diluent gas through an oxidative dehydrogenation reactor, and oxidative dehydrogenation is performed therein to produce a reaction product separating water from the reaction product condensing hydrocarbons to produce a crude hydrocarbon mixture; and separating butadiene from the crude hydrocarbon mixture, where a gas containing n-butane remaining after the butadiene is separated is fed into the oxidative dehydrogenation reactor, and butane is used as a diluent gas. Because butane is used as a diluent gas, a C4 mixture and gas products may be easily separated through cooling and condensation processes. Thus, the method may increase pro- (Continued)

ductivity while reducing energy consumption and raw material costs, thereby improving economic efficiency.

10 Claims, 3 Drawing Sheets

(51) Int. Cl.

| | | |
|---|---|---|
| *C07C 7/00* | (2006.01) | |
| *C07C 7/04* | (2006.01) | |
| *C07C 7/09* | (2006.01) | |
| *B01J 8/02* | (2006.01) | |
| *B01D 5/00* | (2006.01) | |
| *B01D 19/00* | (2006.01) | |

(52) U.S. Cl.
CPC ......... *B01D 5/006* (2013.01); *B01D 19/0068* (2013.01); *B01J 8/0278* (2013.01); *B01J 8/0285* (2013.01); *C07C 7/005* (2013.01); *C07C 7/04* (2013.01); *C07C 7/09* (2013.01); *B01J 2208/00176* (2013.01)

(56) References Cited

U.S. PATENT DOCUMENTS

| | | | |
|---|---|---|---|
| 4,504,692 | A | 3/1985 | Arakawa et al. |
| 10,421,700 | B2 * | 9/2019 | Josch .................. C07C 7/11 |
| 2007/0244349 | A1 | 10/2007 | Crone et al. |
| 2014/0163290 | A1 * | 6/2014 | Grune .................. C07C 5/48 |
| | | | 585/626 |
| 2014/0200381 | A1 | 7/2014 | Josch et al. |
| 2015/0166439 | A1 * | 6/2015 | Bozzano .............. C07C 1/20 |
| | | | 585/252 |
| 2016/0002126 | A1 * | 1/2016 | Caciula ................ C07C 2/10 |
| | | | 585/326 |
| 2016/0152531 | A1 | 6/2016 | Walsdorff et al. |
| 2016/0152532 | A1 * | 6/2016 | Grune .................. C07C 7/11 |
| | | | 585/626 |
| 2016/0355450 | A1 * | 12/2016 | Grune ............... B01J 23/002 |
| 2018/0072638 | A1 * | 3/2018 | Josch .................. C07C 5/48 |
| 2018/0105479 | A1 * | 4/2018 | Josch ............... C07C 11/167 |
| 2019/0016650 | A1 * | 1/2019 | Josch ................ C07C 7/005 |
| 2019/0031580 | A1 * | 1/2019 | Kim .................... C07C 7/12 |
| 2019/0330126 | A1 * | 10/2019 | Lee .................... C07C 5/48 |

FOREIGN PATENT DOCUMENTS

| | | |
|---|---|---|
| JP | 2016527224 | 9/2016 |
| KR | 10-2012-0103759 | 9/2012 |
| KR | 10-1256247 | 4/2013 |
| KR | 10-2015-0062934 | 6/2015 |
| KR | 10-2016-0067425 | 6/2016 |
| KR | 10-1655557 | 9/2016 |
| WO | 2015-051028 | 4/2015 |
| WO | 2016071268 | 5/2016 |

* cited by examiner

METHOD OF PREPARING BUTADIENE

CROSS-REFERENCE TO RELATED APPLICATION

This application is a National Stage Application of International Application No. PCT/KR2017/014966 filed on Dec. 18, 2017, which claims priority to Korean Patent Application No. 10-2016-0182471, filed on Dec. 29, 2016 in the Korean Intellectual Property Office, the disclosure of which is incorporated herein by reference.

TECHNICAL FIELD

The present invention relates to a method of preparing butadiene. More specifically, the present invention relates to a method of preparing butadiene, which enables preparation of high-purity butadiene through economically efficient processes capable of increasing productivity while reducing energy consumption and raw material costs.

BACKGROUND ART

Butadiene, an important basic fraction, is used as an intermediary for various petrochemical products, and demand and value thereof are gradually increasing in the petrochemical market.

Butadiene can be extracted from the C4 fraction through naphtha cracking or obtained by direct dehydrogenation or oxidative dehydrogenation of butene.

Thereamong, according to the method of preparing butadiene through oxidative dehydrogenation of butene, oxygen is used as a reactant, and two hydrogens are removed from butene to generate butadiene. In this case, water generated as a result of the reaction is stable. Thus, the method is thermodynamically very advantageous. In addition, since oxidative dehydrogenation is an exothermic reaction unlike direct dehydrogenation, butadiene may be obtained in high yield even at low reaction temperature as compared with direct dehydrogenation. Therefore, using the method of preparing butadiene through oxidative dehydrogenation of butene, it is possible to effectively meet increasing demand for butadiene.

In addition, according to the method of preparing butadiene through oxidative dehydrogenation of butene, in addition to raw materials, nitrogen, steam, or the like is added as a diluent gas for the purpose of reducing explosion risk due to oxygen and for removal of heat of reaction. However, when hydrocarbons including butadiene are separated from reaction products including nitrogen and very low temperature gases using a process of liquefying hydrocarbons, a very low temperature refrigerant is required, which causes an excessive increase in cost.

For this reason, an absorption process in which a solvent is used is mainly used to separate hydrocarbons. In this regard, FIGS. 1a and 1b include schematic diagrams for explaining conventional devices for preparing butadiene and conventional methods of preparing butadiene.

Referring to FIGS. 1a and 1b, the conventional device may include a cooling separation part 120 responsible for separating water from oxidative dehydrogenation reaction products consisting of a butadiene-containing C4 mixture and gas products, which are obtained through oxidative dehydrogenation of reaction raw materials containing butene, oxygen ($O_2$), steam, and a diluent gas, which are fed into an oxidative dehydrogenation reaction part 110; an absorption separation part 130 responsible for separating COx, $O_2$, and $N_2$ used as a diluent gas from the oxidative dehydrogenation reaction products, from which water is separated; and a purification part 140 responsible for separating butadiene from a stream containing butadiene excluding COx, $O_2$, and $N_2$ used as a diluent gas, which are separated in the absorption separation part 130. In this case, in the absorption separation part 130, a solvent capable of absorbing butadiene, unreacted butene, and butane included in the raw materials or a solvent capable of selectively absorbing butadiene may be used.

The oxidative dehydrogenation reaction part 110 may be operated under isothermal or adiabatic conditions, in which case a gas containing butene, oxygen ($O_2$), steam, and n-butane is used as a reaction raw material and a ferrite catalyst is used as a catalyst, wherein n-butane is a residue remaining after butadiene is separated in the purification part and is fed again into the oxidative dehydrogenation reaction part.

The cooling separation part 120 may be operated by a quenching-type direct cooling system (quencher) or an indirect cooling system.

FIGS. 1a and 1b show examples of selectively absorbing/separating butadiene in the absorption separation part 130. However, the absorption separation part 130 may be also operated according to an absorption manner using a solvent capable of selectively absorbing butadiene from reaction products from which water is separated, or a solvent capable of absorbing all hydrocarbons including a C4 mixture. Specific examples of solvents capable of selectively absorbing butadiene may include acetonitrile (ACN), N-methylpyrrolidone (NMP), dimethyl formamide (DMF), and the like, and specific examples of solvents capable of absorbing all hydrocarbons including a C4 mixture may include toluene, xylene, and the like. In the absorption separation part 130, COx, $O_2$, $N_2$ used as a diluent gas are incinerated.

For example, a conventional butadiene purification apparatus may be used as the purification part 140. When necessary, an acetonitrile (ACN) process, a N-methylpyrrolidone (NMP) process, or a dimethyl formamide (DMF) process may be performed to purify butadiene.

However, since a large amount of energy is consumed to recover a solvent used in the absorption separation process, there is an urgent need to develop related technologies that can improve economic efficiency of processes.

PRIOR ART DOCUMENT

[Patent Document](Patent Document 1) KR 10-2012-0103759 A

DISCLOSURE

Technical Problem

Therefore, the present invention has been made in view of the above problems, and it is one object of the present invention to provide a method of preparing butadiene, which enables preparation of high-purity butadiene through economically efficient processes. According to the method of the present invention, since butane is used instead of nitrogen as a diluent gas in preparation of butadiene through oxidative dehydrogenation of butene, a C4 mixture and gas products may be easily separated through cooling and condensation processes. Thus, use of the method of the present invention may increase productivity while reducing energy consumption and raw material costs.

The above and other objects can be accomplished by the present disclosure described below.

Technical Solution

In accordance with one aspect of the present invention, provided is a method of preparing butadiene, including a step, in which reaction raw materials containing butene, oxygen ($O_2$), steam, and a diluent gas are passed through an oxidative dehydrogenation reaction part, and oxidative dehydrogenation is performed therein;

a step of separating water from a butadiene-containing C4 mixture and gas products, which are generated in the oxidative dehydrogenation reaction, by passing the butadiene-containing C4 mixture and the gas products through a cooling separation part;

a step of condensing hydrocarbons by passing the butadiene-containing C4 mixture and the gas products, from which water is separated, through a condensation separation part; and a step of separating butadiene by passing a C4 mixture including hydrocarbons condensed in the condensation separation part through a purification part, wherein a gas containing n-butane remaining after butadiene is separated in the purification part is fed again into the oxidative dehydrogenation reaction part, and the diluent gas is butane.

Advantageous Effects

As apparent from the foregoing, the present invention advantageously provides a method of preparing butadiene, which enables preparation of high-purity butadiene through economically efficient processes. According to the present invention, unlike conventional methods, in which nitrogen is used as a diluent gas and an absorption process is used to separate butadiene from reaction products, since butane is used instead of nitrogen as a diluent gas in preparation of butadiene through oxidative dehydrogenation of butene, a C4 mixture and gas products excluding butadiene can be easily separated through a condensation process. Thus, use of the method of the present invention can increase productivity while reducing energy consumption and raw material costs.

BEST MODE

Hereinafter, the method of preparing butadiene and the device for preparing the same according to the present invention will be described in detail. According to the present invention, to prepare butadiene through economically efficient processes, butane is used as a diluent gas, a condensation separation process is used, and a recirculation stream, in which gases containing n-butane and butene excluding butadiene, which are separated in a purification part, are introduced into an oxidative dehydrogenation reaction part, is applied. When the condensation separation process is used, a C4 mixture and gas products as oxidative dehydrogenation reaction products may be easily separated even when an absorption separation process is omitted, and process load and energy consumption may be reduced through heat exchange.

Figure 2:
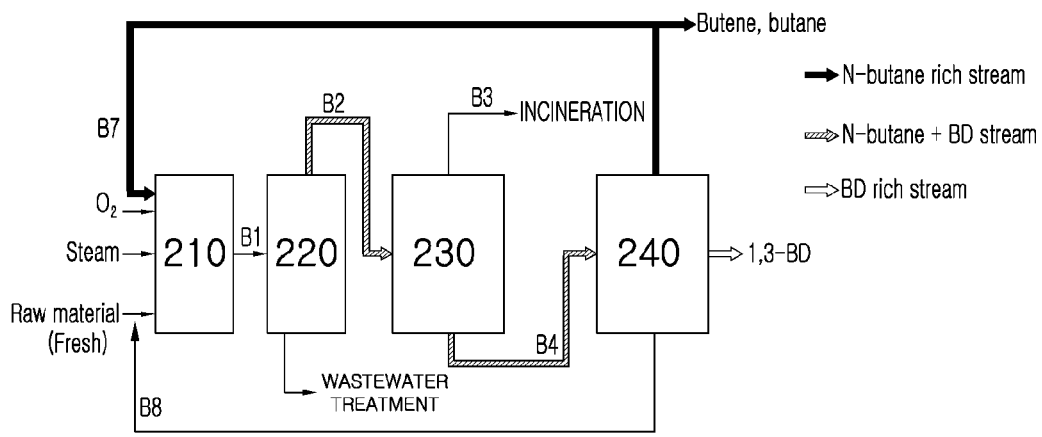
FIGS. 2 to 4 include schematic diagrams for explaining the device for preparing butadiene and the method of preparing the same according to the present invention.
Figure 3:
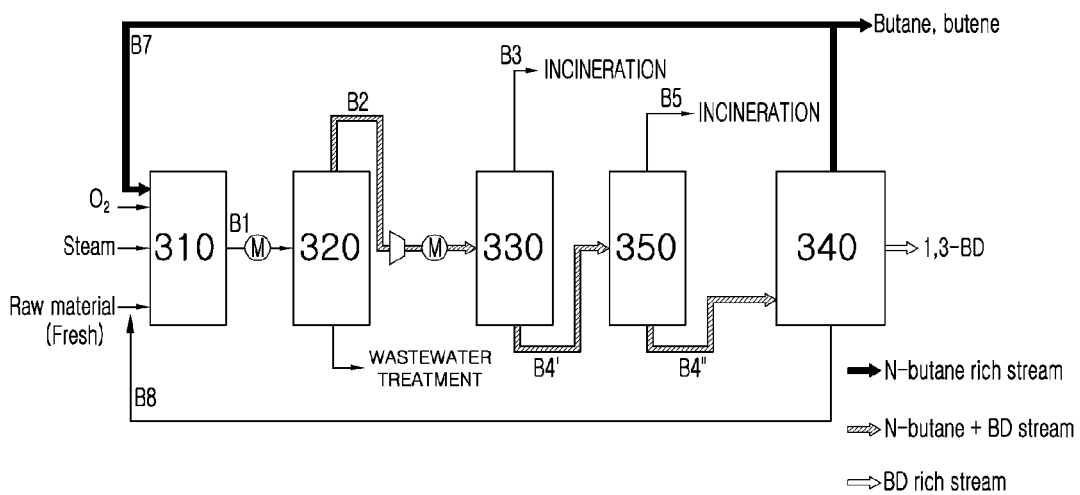
Figure 4:
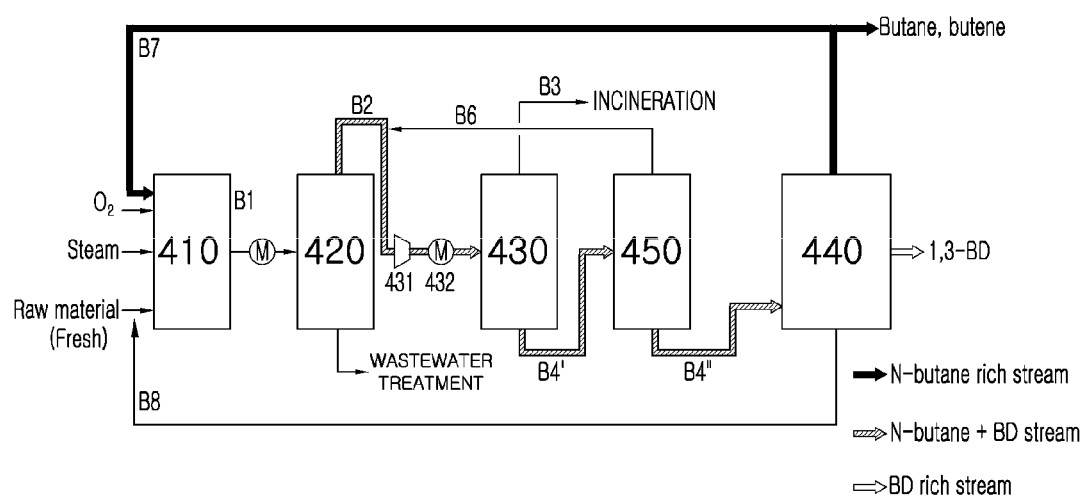

Hereinafter, the method of preparing butadiene and the device for preparing the same according to the present invention will be described in detail with reference to drawings. FIGS. 2 to 4 include schematic diagrams for explaining the device for preparing butadiene and the method of preparing the same according to the present invention.

Referring to FIG. 2, first, reaction raw materials containing butene, oxygen ($O_2$), steam, and a diluent gas (butane) are passed through an oxidative dehydrogenation reaction part 210 to generate a butadiene-containing C4 mixture and gas products, and a stream B1 discharged from the oxidative dehydrogenation reaction part 210 is then introduced into a cooling separation part 220 to separate water. At this time, the reaction raw materials are combined with a discharge stream B7 generated after a purification process, and introduced into the oxidative dehydrogenation reaction part 210. For example, oxygen ($O_2$) is preferably introduced into the reaction raw materials in a gaseous form having a purity of 90% or more, 95% or more, or 98% or more. In the stream B1 discharged after the oxidative dehydrogenation process, butadiene, n-butane, butene, $O_2$, COx, $H_2O$, and the like may be contained.

A discharge stream B2 generated after the cooling separation process may be introduced into a condensation separation part 230. The discharge stream B2 may contain butadiene, n-butane, butene, $O_2$, COx, and the like.

The discharge stream B2 generated after the cooling separation process is passed through the condensation separation part 230, so that hydrocarbons are condensed. A discharge stream B4 generated after the condensation separation process is introduced into a purification part 240. The discharge stream B4 may contain crude hydrocarbons including n-butane, butene, and butadiene, which are condensed in the condensation separation part 230, and the discharge stream B4 may be introduced into the purification part 240 to purify butadiene. The discharge stream B7 generated after the purification process may contain a large amount of residual n-butane, and is fed again into the oxidative dehydrogenation reaction part 210, resulting in formation of a recirculation stream.

Another discharge stream B3 generated after the condensation separation process may contain hydrocarbons, COx, $O_2$, and the like, which are not condensed when hydrocarbons are condensed using cooling water through compression/cooling in the condensation separation process.

A discharge stream B8 containing butene remaining after butadiene is separated in the purification part 240 may be mixed with freshly supplied butene, and then fed into the oxidative dehydrogenation reaction part 210. In this case, reaction processes may continuously proceed, thereby improving economic efficiency.

Herein, the term "crude hydrocarbons" refer to crude hydrocarbons commonly used in the art to which the present invention pertains, and unless otherwise specified herein, refer to a mixture containing a large amount of n-butane, butene, and butadiene and a small amount of hydrocarbons having a boiling point higher than those thereof.

Herein, the term "COx" refers to, unless otherwise specified herein, CO, $CO_2$, or a mixture thereof.

The C4 mixture refers to, unless otherwise specified herein, a mixture of butane contained in raw materials, unreacted butene, and generated butadiene.

In the present invention, butene may be 1-butene, 2-butene, or a mixture thereof. Raw material gases containing butene generally used to prepare butadiene are not particularly limited and may be used as the raw material gases containing butene of the present invention.

For example, butene may be obtained from a hydrocarbon mixture including butenes, such as raffinate-2 and raffinate-3, included in the C4 fraction produced when a high-purity butene gas and naphtha are decomposed.

The steam is a gas which is injected for the purpose of preventing coking of a catalyst and removing heat of reaction while reducing risk of explosion of reactants when oxidative dehydrogenation is performed.

In the present invention, oxygen ($O_2$) reacts with butene as an oxidizing agent to cause dehydrogenation.

Any catalysts may be used as the catalyst of the present invention packed in the reactor without any particular limitation as long as the catalysts are capable of catalyzing oxidative dehydrogenation of butene to prepare butadiene. For example, ferrite catalysts or bismuth molybdate catalysts may be included.

In one embodiment of the present invention, the catalyst may be a ferrite catalyst. In particular, when zinc ferrite, magnesium ferrite, or manganese ferrite is used, selectivity for butadiene may be increased. The kind and amount of the reaction catalyst may vary depending on specific reaction conditions.

The diluent gas may be butane.

For example, the oxidative dehydrogenation reaction part 210 may be operated under isothermal or adiabatic conditions, in which case butene, oxygen ($O_2$), steam, and a gas containing n-butane are used as reaction raw materials, and a ferrite catalyst is used as a catalyst, wherein n-butane is a residue remaining after butadiene is separated in the purification part 240 and is fed again into the oxidative dehydrogenation reaction part.

For example, oxygen ($O_2$) contained in the reaction raw materials may be fed in a gaseous form having a purity of 90% or more, 95% or more, or 98% or more.

Feeding of oxygen ($O_2$) in a gaseous form having a purity of 90% or more means that oxygen is not supplied from air, but is fed in a pure oxygen form. Thus, by measuring the amount of active ingredients contained in reaction raw materials in real time, it is possible to control the amount of each of the components contained in reaction raw materials fed into a reactor.

For example, in the oxidative dehydrogenation reaction part 210, oxidative dehydrogenation may be performed in a molar ratio of butene:oxygen:steam:diluent gas (n-butane) =1:0.5 to 5:0.1 to 20:0.1 to 20. Within this range, energy consumption and raw material costs may be reduced, and productivity may be improved, thereby increasing economic efficiency of processes.

As a particular example, the oxidative dehydrogenation reaction part 210 is preferably operated in a molar ratio of oxygen:butene=1:0.3 to 3, a molar ratio of steam:butene=1: 0.1 to 20, and a molar ratio of n-butane:butene=1:0.1 to 20 at a reaction pressure of atmospheric pressure to 10 atm and a reaction temperature of 150 to 650° C. under isothermal or adiabatic conditions. Within this range, energy consumption and raw material costs may be reduced, and productivity may be improved, thereby increasing economic efficiency of processes.

For example, the cooling separation part 220 may be operated by a quenching-type direct cooling system (quencher) or an indirect cooling system. In this case, the cooling separation part may be rapidly cooled to a temperature of 0 to 50° C.

For example, the condensation separation part 230 may have a single-stage compression structure having one stage or a multistage compression structure having 2 to 10 stages or 1 to 2 stages. When compressing from an initial pressure to a target pressure, a lot of power is required. In addition, heat is generated due to gas compression, which causes gas expansion, resulting in poor compression efficiency. Therefore, to prevent such problems, multistage compression is performed. In this case, heat generated in the compression process may be dissipated using a cooler.

In the condensation separation part 230, condensation conditions may be determined so that the stream of the condensation separation part 230 is out of an explosive range in consideration of unreacted oxygen (i.e., above upper explosive limit or below limiting oxygen concentration).

In one embodiment of the present invention, a refrigerant used in the condensation separation part 230 may be one or more selected from the group consisting of cooling water, ethylene glycol, an aqueous solution of ethylene glycol having a concentration of 20 to 100% by weight, propylene glycol, an aqueous solution of propylene glycol having a concentration of 30 to 100% by weight, and a propylene-based solvent. For example, the propylene-based solvent, as a compound including propylene or propylene, may have a boiling point of −10° C. or less or −10 to −50° C.

As a particular example, the refrigerant may be cooling water, cooling water having a temperature of 0 to 40° C., or cooling water having a temperature of 5 to 30° C. In this case, the extrusion discharge temperature may be 250° C. or less or 50 to 250° C., and the cooling temperature of a compression discharge stream may be 120° C. or less or 20 to 80° C.

Conventionally, since nitrogen is used as a diluent gas, a very low-temperature refrigerant is required when gas products are separated using a general distillation method. In the present invention, since butane is used as a diluent gas, a lower grade of refrigerant may be used.

Heat generated when COx and $O_2$ separated in the condensation separation part 230 are incinerated may be reused to heat raw materials, or reused in the purification part.

A conventional apparatus for purifying butadiene may be used as the purification part 240. When necessary, a process capable of using separating butadiene, such as an acetonitrile (ACN) process, a N-methylpyrrolidone (NMP) process, or a dimethyl formamide (DMF) process, may be performed.

In a purification step, solvents, high boiling point components, and low boiling point components are removed from crude hydrocarbons including n-butane and butadiene, which are obtained in the coagulation separation, and thus high-purity butadiene may be obtained.

In one embodiment of the present invention, the purity of finally obtained butadiene through the series of steps described above may be 95.0 to 99.9%.

FIG. 3 is a schematic diagram showing a process, in which gases contained in hydrocarbons condensed in the condensation separation part in FIG. 2 are separated in a degasification part. Through the process, all hydrocarbons may be condensed/separated and then absorbed/recovered.

For example, the degasification part may be operated by stripping using a conventional column, or degasification.

Referring to FIG. 3, first, reaction raw materials containing butene, oxygen ($O_2$), steam, and a diluent gas (butane) are passed through an oxidative dehydrogenation reaction part 310, so that a butadiene-containing C4 mixture and gas products are generated, and the stream B1 discharged after the oxidative dehydrogenation process is introduced into a cooling separation part 320. At this time, reaction raw materials are combined with the discharge stream B7 generated after the purification process, and introduced into the oxidative dehydrogenation reaction part 310. The stream B1 discharged after the oxidative dehydrogenation process may contain butadiene, n-butane, butene, $O_2$, COx, $H_2O$, and the like. The stream B1 is introduced into the cooling separation part 320 to separate water.

The discharge stream B2 generated after the cooling separation process may contain butadiene, n-butane, butene, $O_2$, COx, and the like. The discharge stream B2 is introduced into a condensation separation part 330 to condense hydrocarbons.

A discharge stream B4' generated after the condensation separation process may contain hydrocarbons including butadiene, n-butane, butene, and the like. The discharge stream B4' is introduced into a degasification part 350 to separate COx and $O_2$. Another discharge stream B3 generated after the condensation separation process may contain COx, $O_2$, and uncondensed hydrocarbons.

A discharge stream B4" generated after the degasification process may contain crude hydrocarbon including n-butane, butene, and butadiene excluding COx and $O_2$, which are separated in the degasification part. The discharge stream B4" is introduced into a purification part 340. Thus, butadiene may be efficiently purified. Another discharge stream B5 generated after the degasification process may contain separated COx and $O_2$, and may be incinerated in a later process.

The discharge stream B7 generated after the purification process may contain a large amount of residual n-butane, and is fed into the oxidative dehydrogenation reaction part 310, resulting in formation of a recirculation stream.

The discharge stream B8 containing butene remaining after butadiene is separated in the purification part 340 is mixed with freshly supplied butene, and fed into the oxidative dehydrogenation reaction part 310, resulting in formation of a recirculation stream.

A heat exchange means may be provided between the condensation separation part and the oxidative dehydrogenation reaction part, between the condensation separation part and the degasification part, or between the condensation separation part, the oxidative dehydrogenation reaction part, and the degasification part, so that heat generated when COx and $O_2$ separated in the condensation separation part are incinerated, or heat generated when COx and $O_2$ separated in the degasification part are incinerated is reused to heat raw materials, or reused in the purification part.

FIG. 4 is a schematic diagram showing a case where the discharge stream B5 generated after the degasification process in FIG. 3 is fed again into the condensation system, and thus a discharge stream B6 is circulated to a condensation separation part 430. In this case, gas separation efficiency may be improved by circulating COx and separated in a degasification part 450 to the condensation separation part 430.

Referring to FIG. 4, first, reaction raw materials containing butene, oxygen ($O_2$), steam, and a diluent gas (butane) are passed through an oxidative dehydrogenation reaction part 410, so that a butadiene-containing C4 mixture and gas products are generated from oxidative dehydrogenation reaction products, and the stream B1 discharged after the oxidative dehydrogenation process is introduced into a cooling separation part 420. At this time, the reaction raw materials are combined with the discharge stream B7 generated after the purification process, and introduced into the oxidative dehydrogenation reaction part 410.

The stream B1 discharged after the oxidative dehydrogenation process may contain butadiene, n-butane, butene, $O_2$, COx, $H_2O$, and the like. The stream B1 is introduced into the cooling separation part 320 to separate water.

The discharge stream B2 generated after the cooling separation process may contain butadiene, n-butane, butene, $O_2$, COx, and the like. The discharge stream B2 is introduced into the condensation separation part 330 to condense hydrocarbons.

The discharge stream B4' generated after the condensation separation process may contain hydrocarbons including butadiene, n-butane, butene, and the like. The discharge stream B4' is introduced into the degasification part 450 to separate COx and $O_2$.

Another discharge stream B3 generated after the condensation separation process may contain COx, $O_2$, and uncondensed hydrocarbons.

COx and $O_2$ additionally separated in the degasification part 450 may be fed into the condensation system through the discharge stream B6 generated after the degasification process, and may then be recondensed and separated in the condensation separation part 430. Another discharge stream B4" generated after the degasification process may contain crude hydrocarbons including n-butane, butene, and butadiene excluding COx and $O_2$, which are separated in the degasification part 450. The crude hydrocarbons are introduced in a purification part 440. Thus, butadiene may be efficiently purified.

The discharge stream B7 generated after the purification process may contain a large amount of residual n-butane, and is fed into the oxidative dehydrogenation reaction part 410, resulting in formation of a recirculation stream.

The discharge stream B8 containing residual butene remaining after butadiene is separated in the purification part 440 is mixed with freshly supplied butene, and fed into the oxidative dehydrogenation reaction part 410, resulting in formation of a recirculation stream.

Heat generated when COx and $O_2$ are incinerated in the condensation separation part 430 may be reused to heat raw materials, or reused in the purification part.

For example, a device used in the method of the present invention, referring to FIG. 2, includes the oxidative dehydrogenation reaction part 210, in which oxidative dehydrogenation of reaction raw materials containing butene, oxygen ($O_2$), steam, and a diluent gas (butane) is performed; the cooling separation part 220 responsible for separating water from a butadiene-containing C4 mixture and gas products, which are generated through the oxidative dehydrogenation reaction process; the condensation separation part 230 responsible for condensing hydrocarbons from the butadiene-containing C4 mixture and the gas products, from which water is separated; and the purification part 240 responsible for separating butadiene from crude hydrocarbons including n-butane, butene, and butadiene, which are condensed in the condensation separation part 230, wherein these parts are configured to have the discharge stream B7 and the discharge stream B8, wherein the discharge stream B7 is responsible for refeeding a gas containing n-butane excluding butadiene, which are separated in the purification part 240, into the oxidative dehydrogenation reaction part 210, and the discharge stream B8 is responsible for refeeding butene excluding butadiene, which are separated from crude hydrocarbons in the purification part 240, into the oxidative dehydrogenation reaction part 210.

As another example, a device for preparing butadiene, referring to FIG. 3, includes the oxidative dehydrogenation reaction part 210, in which oxidative dehydrogenation of reaction raw materials containing butene, oxygen ($O_2$), steam, and a diluent gas (butane) is performed; the cooling separation part 320 responsible for separating water from a butadiene-containing C4 mixture and gas products, which are generated in the oxidative dehydrogenation reaction; the condensation separation part 330 responsible for condensing hydrocarbons from the butadiene-containing C4 mixture and the gas products, from which water is separated; the degasification part 350 responsible for separating COx and $O_2$ and crude hydrocarbons including n-butane, butene, and butadiene in a C4 mixture containing hydrocarbons condensed in a condensation separation part 320; and the purification part 340 responsible for separating butadiene from crude hydrocarbons including n-butane, butene, and butadiene, which are separated in the degasification part 350, wherein these parts are configured to have the discharge stream B7 and the discharge stream B8, wherein the discharge stream B7 is responsible for refeeding a gas containing n-butane excluding butadiene, which are separated from crude hydrocarbons in the purification part 340, into the oxidative dehydrogenation reaction part 310, and the discharge stream B8 is responsible for mixing butene excluding butadiene, which are separated from crude hydrocarbons in the purification part 340, with freshly supplied butane, and refeeding the mixture into the oxidative dehydrogenation reaction part 310.

As another example, a device for preparing butadiene, referring to FIG. 4, includes the oxidative dehydrogenation reaction part 410, in which oxidative dehydrogenation of reaction raw materials containing butene, oxygen ($O_2$), steam, and a diluent gas (butane) is performed; the cooling separation part 420 responsible for separating water from a butadiene-containing C4 mixture and gas products, which are obtained through the oxidative dehydrogenation; the condensation separation part 430 responsible for condensing hydrocarbons from the butadiene-containing C4 mixture and the gas products, from which water is separated; and the degasification part 450 responsible for separating COx and $O_2$ and crude hydrocarbons including n-butane, butene, and butadiene in the C4 mixture containing hydrocarbons condensed in a condensation separation part 420, wherein these parts are configured to have the discharge stream B4", the discharge stream B7, and the discharge stream B8, wherein the discharge stream B4" is responsible for feeding crude hydrocarbons including n-butane, butene, and butadiene, which are separated in the degasification part 450, into the purification part 440 to separate butadiene, the discharge stream B7 is responsible for refeeding a gas containing n-butane excluding butadiene, which are separated in the purification part 440, into the oxidative dehydrogenation reaction part 410, and the discharge stream B8 is responsible for refeeding butene excluding butadiene, which are separated from crude hydrocarbons in the purification part 440, into the oxidative dehydrogenation reaction part 410.

The device is configured so that the discharge stream B6 containing COx and $O_2$, which are separated in the degasification part 450, is fed into the condensation system, so that the discharge stream B6 is circulated to the condensation separation part 430.

Unless otherwise specified herein, the condensation system refers to a system including a compressor 431, a heat exchanger 432, and the condensation separation part 430.

Heat generated when COx and $O_2$ separated in the condensation separation part are incinerated may be reused to heat raw materials, or reused in the purification part.

A heat exchange means may be provided between the condensation separation parts 230, 330, and 430 and the oxidative dehydrogenation reaction parts 210, 310, and 410, between the condensation separation parts 230, 330, and 430 and the degasification parts 350 and 450, or between the condensation separation parts 230, 330, and 430, the oxidative dehydrogenation reaction parts 210, 310, and 410, and the degasification parts 350 and 450, so that heat generated when COx and $O_2$ separated in the condensation separation parts 230, 330, and 430 are incinerated, or heat generated when COx and $O_2$ separated in the degasification parts 350 and 450 are incinerated is reused to heat raw materials, or reused in the purification parts 240, 340, and 440.

In summary, when the method of preparing butadiene and the device for preparing the same according to the present invention are used, the drawbacks of conventional butadiene preparation methods, in which nitrogen is used as a diluent gas, may be compensated, and process efficiency may be improved. That is, use of the method and device of the present invention may maximize energy efficiency by minimizing the amount of energy consumed in preparation processes. In addition, since the method of preparing butadiene according to the present invention may be directly used for purification/separation of various materials (ACN, NMP, DMF, and the like) described above, the method of the present invention may be applied to various processes.

Hereinafter, the present invention will be described in more detail with reference to the following preferred examples. However, these examples are provided for illustrative purposes only and should not be construed as limiting the scope and spirit of the present invention. In addition, it will be apparent to those skilled in the art that various changes and modifications may be made without departing from the spirit and scope of the present invention, and such changes and modifications are also within the scope of the appended claims.

EXAMPLE

Example 1

Butadiene was prepared from butene using butane as a diluent gas using a device shown in FIG. 2. oxidative dehydrogenation of reaction raw materials containing 78% by weight of butene and 22% by weight of butane is performed in a molar ratio of butene:oxygen:steam:diluent gas (n-butane)=1:0.75:5:2.8. Condensation was performed at a pressure of 8 KSCG and a cooling temperature of 35° C. in the condensation separation part. In the condensation separation part and the purification part, DMF was used as a solvent.

In this case, a discharge stream generated through oxidative dehydrogenation was analyzed using gas chromatography. The compositions of discharge streams B1, B2, B3, B4, B7, and B8 of each of the cooling separation part, the condensation separation part, and the purification part were calculated using a process simulator (AspenPlus), and the results are shown in Tables 1 and 2. In addition, the amounts of energy used in each of the condensation separation part and the purification part were calculated using a process simulator, and the results are shown in Table 5.

Comparative Example 1

Figure 1A:
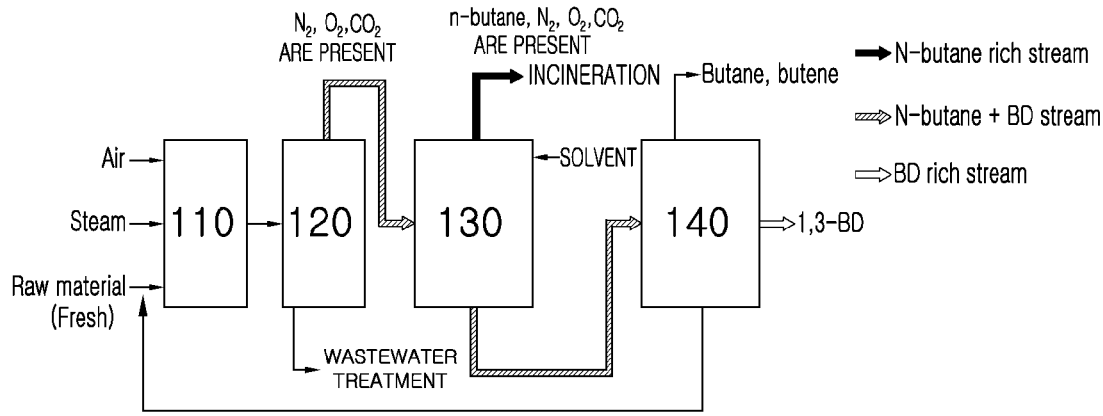
FIGS. 1a and 1b include schematic diagrams for explaining conventional devices for preparing butadiene and methods of preparing the same.
Figure 1B:
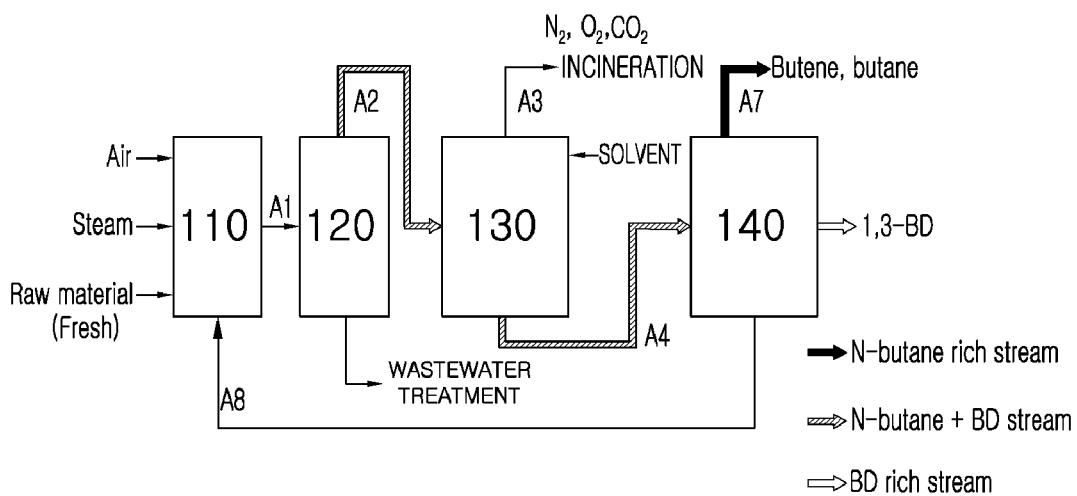

Butadiene was prepared from butene using nitrogen as a diluent gas using devices shown in FIGS. 1a and 1b. In this case, except that, in the absorption separation part, an operating pressure was set at 3 KSCG and a cooling temperature was set at 5° C., and, in absorption separation part and the purification part, DMF was used a solvent, experiments were performed in the same manner as in Example 1.

In this case, a discharge stream generated through oxidative dehydrogenation was analyzed using gas chromatography. The compositions of discharge streams A1, A2, A3, A4, A7, and A8 of each of the cooling separation part, the condensation separation part, and the purification part were calculated using a process simulator (AspenPlus), and the results are shown in Tables 3 and 4 below. The flow rate of butadiene (A4) sent to the purification part when butadiene was recovered using a solvent was the same as that in Example 1.

In addition, the amounts of energy used in each of the condensation separation part and the purification part were calculated using a process simulator, and the results are shown in Table 5.

TABLE 1

| Classification | MW | B1 kg/hr | wt % | B2 kg/hr | wt % | B3 kg/hr | wt % |
|---|---|---|---|---|---|---|---|
| $N_2$ | 28.0 | 0.0 | 0.0 | 0.0 | 0.0 | 0.0 | 0.0 |
| $CO_2$ | 44.0 | 120.0 | 2.0 | 120.0 | 3.0 | 120.0 | 32.4 |
| CO | 28.0 | 39.0 | 0.7 | 39.0 | 1.0 | 39.0 | 10.5 |
| $O_2$ | 32.0 | 21.0 | 0.4 | 21.0 | 0.5 | 21.0 | 5.7 |
| Butane | 58.1 | 2921.6 | 49.1 | 2921.6 | 73.1 | 146.1 | 39.4 |
| 1,3-Butadiene | 54.1 | 745.7 | 12.5 | 745.7 | 18.7 | 37.3 | 10.1 |
| Butene | 56.1 | 150.0 | 2.5 | 150.0 | 3.8 | 7.5 | 2.0 |
| HB | 72.1 | 29.4 | 0.5 | 0.0 | 0.0 | 0.0 | 0.0 |
| Water | 18.0 | 1928.0 | 32.4 | 0.0 | 0.0 | 0.0 | 0.0 |
| Sum | | 5954.8 | 100 | 3997.4 | 100 | 370.9 | 100 |

TABLE 2

| Classification | B4 kg/hr | wt % | B7 kg/hr | wt % | B8 kg/hr | wt % | 1,3-BD kg/hr | wt % |
|---|---|---|---|---|---|---|---|---|
| $N_2$ | 0.0 | 0.0 | 0.0 | 0.0 | 0.0 | 0.0 | 0.0 | 0.0 |
| $CO_2$ | 0.0 | 0.0 | 0.0 | 0.0 | 0.0 | 0.0 | 0.0 | 0.0 |
| CO | 0.0 | 0.0 | 0.0 | 0.0 | 0.0 | 0.0 | 0.0 | 0.0 |
| $O_2$ | 0.0 | 0.0 | 0.0 | 0.0 | 0.0 | 0.0 | 0.0 | 0.0 |
| Butane | 2775.5 | 76.5 | 277.5 | 99.2 | 0.0 | 0.0 | 0.0 | 0.0 |
| 1,3-Butadiene | 708.4 | 19.5 | 7.1 | 0.3 | 7.1 | 5.4 | 694.6 | 99.5 |
| Butene | 142.5 | 3.9 | 14.3 | 0.5 | 124.8 | 94.6 | 3.5 | 0.5 |
| HB | 0.0 | 0.0 | 0.0 | 0.0 | 0.0 | 0.0 | 0.0 | 0.0 |
| Water | 0.0 | 0.0 | 0.0 | 0.0 | 0.0 | 0.0 | 0.0 | 0.0 |
| Sum | 3626.5 | 100 | 2796.9 | 100 | 131.8 | 100 | 697.7 | 100 |

TABLE 3

| Classification | MW | A1 kg/hr | wt % | A2 kg/hr | wt % | A3 kg/hr | wt % |
|---|---|---|---|---|---|---|---|
| $N_2$ | 28.0 | 1268.7 | 27.6 | 1268.7 | 48.2 | 1268.7 | 77.4 |
| $CO_2$ | 44.0 | 120.0 | 2.6 | 120.0 | 4.6 | 120.0 | 7.3 |
| CO | 28.0 | 39.0 | 0.9 | 39.0 | 1.5 | 39.0 | 2.4 |
| $O_2$ | 32.0 | 21.0 | 0.5 | 21.0 | 0.8 | 21.0 | 1.3 |
| Butane | 58.1 | 290.0 | 6.3 | 290.0 | 11.0 | 146.1 | 8.9 |
| 1,3-Butadiene | 54.1 | 745.7 | 16.2 | 745.7 | 28.3 | 37.3 | 2.3 |
| Butene | 56.1 | 150.5 | 3.3 | 150.5 | 5.7 | 7.5 | 0.5 |
| HB | 72.1 | 29.4 | 0.6 | 0.0 | 0.0 | 0.0 | 0.0 |
| Water | 18.0 | 1928.0 | 42.0 | 0.0 | 0.0 | 0.0 | 0.0 |
| Sum | | 4591.8 | 100 | 2634.5 | 100 | 1639.6 | 100 |

TABLE 4

| Classification | A4 kg/hr | wt % | A7 kg/hr | wt % | A8 kg/hr | wt % | 1,3-BD kg/hr | wt % |
|---|---|---|---|---|---|---|---|---|
| $N_2$ | 0.0 | 0.0 | 0.0 | 0.0 | 0.0 | 0.0 | 0.0 | 0.0 |
| $CO_2$ | 0.0 | 0.0 | 0.0 | 0.0 | 0.0 | 0.0 | 0.0 | 0.0 |
| CO | 0.0 | 0.0 | 0.0 | 0.0 | 0.0 | 0.0 | 0.0 | 0.0 |
| $O_2$ | 0.0 | 0.0 | 0.0 | 0.0 | 0.0 | 0.0 | 0.0 | 0.0 |
| Butane | 143.9 | 14.5 | 143.9 | 87.1 | 0.0 | 0.0 | 0.0 | 0.0 |
| 1,3-Butadiene | 708.4 | 71.2 | 7.1 | 4.3 | 7.1 | 5.4 | 694.3 | 99.5 |
| Butene | 14.25 | 14.3 | 14.3 | 8.6 | 124.8 | 94.6 | 3.5 | 0.5 |
| HB | 0.0 | 0.0 | 0.0 | 0.0 | 0.0 | 0.0 | 0.0 | 0.0 |
| Water | 0.0 | 0.0 | 0.0 | 0.0 | 0.0 | 0.0 | 0.0 | 0.0 |
| Sum | 9948.8 | 100 | 165.2 | 100 | 131.8 | 100 | 697.7 | 100 |

TABLE 5

| | | Example 1 | | Comparative Example 1 | |
|---|---|---|---|---|---|
| Classification | | Condensation separation part 230 | Purification part 240 | Absorption separation part 130 | Purification part 140 |
| Steam | Gcal/hr | 0.1 | 1.0 | 0.2 | 1.5 |
| Refrigerant | Gcal/hr | 0.0 | 0.0 | 0.2 | 0.0 |
| Solvent | Ton/hr | 0.9 | 10.6 | 9.4 | 2.6 |
| Electric power | kW | 104 | 27.2 | 94 | 27.2 |

As shown in Tables 1 to 5, in Example 1 according to the present invention, compared to Comparative Example 1, butadiene of the same purity as Comparative Example 1 is obtained while reducing energy consumption.

In addition, as shown in Table 5, in the case of Example 1, the total amount of the solvent used in the condensation separation part and the purification part is 11.5 ton/hr, whereas in the case of Comparative Example 1, the total amount is 12 ton/hr. That is, in Example 1, as compared with Comparative Example 1, since the solvent is used in a small amount, the amount of steam required in the purification part is reduced, and as a result, energy consumption is reduced, and economic efficiency is increased. Specifically, in Example 1, the total amount of steam used is 1.1 Gcal/hr, and in Comparative Example 1, the total amount of steam used is 1.7 Gcal/hr. The difference between these two values is 0.6 Gcal/hr, which is about 700 kW in terms of kW.

DESCRIPTION OF SYMBOLS

110, 210, 310, 410: OXIDATIVE DEHYDROGENATION REACTION PART
120, 220, 320, 420: COOLING SEPARATION PART
130: ABSORPTION SEPARATION PART
230, 330, 430: CONDENSATION SEPARATION PART
140, 240, 340, 440: PURIFICATION PART 350, 450: DEGASIFICATION PART
431: COMPRESSOR
432: HEAT EXCHANGER

The invention claimed is:

1. A method of preparing butadiene, comprising:

passing reaction raw materials containing butene, oxygen ($O_2$), steam, and a diluent gas consisting essentially of butane through an oxidative dehydrogenation reactor and oxidative dehydrogenation is performed therein to produce a reaction product comprising a butadiene-containing C4 mixture, gas products and water;

separating the water from the butadiene-containing C4 mixture and gas products by passing the reaction product through a cooling separator;

passing the butadiene-containing C4 mixture and the gas products, from which water has been separated, through a condenser to condense hydrocarbons to produce a crude hydrocarbon mixture comprising n-butane, butene, and butadiene; and separating the butadiene from the crude hydrocarbon mixture by passing the crude hydrocarbon mixture through a purification apparatus using acetonitrile (ACN), N-methylpyrrolidone (NMP), or dimethyl formamide (DMF) as a solvent to selectively absorb butadiene, wherein a gas containing n-butane remaining after the butadiene is separated in the purification apparatus is fed into the oxidative dehydrogenation reactor, and wherein, in the oxidative dehydrogenation reactor, oxidative dehydrogenation is performed using the reaction raw materials present in a molar ratio of butene:oxygen:steam:diluent gas of 1:0.5 to 3:0.1 to 20:0.1 to 20, and wherein the step of separating butadiene further comprises, prior to separating the butadiene from the crude hydrocarbon mixture:

separating COx and $O_2$ from the crude hydrocarbon mixture by passing the crude hydrocarbon mixture through a degasification column; and feeding the crude mixture from which the COx and $O_2$ were excluded into the purification apparatus.

2. The method according to claim 1, wherein the oxygen ($O_2$) contained in the reaction raw materials is fed in a gaseous form having a purity of 90% or more.

3. The method according to claim 1, wherein the condenser has a single-stage compression structure having one stage, a multistage compression structure having 2 to 10 stages, or a multistage compression structure having 1 to 2 stages, and, in the condenser, a compression discharge temperature is 50 to 250° C.

4. The method according to claim 1, wherein a refrigerant used in the condenser is one or more selected from the group consisting of cooling water, ethylene glycol, an aqueous solution of ethylene glycol having a concentration of 20 to 100% by weight, propylene glycol, an aqueous solution of propylene glycol having a concentration of 30 to 100% by weight, and a propylene-based solvent.

5. The method according to claim 1, wherein the step of separating butadiene further comprises
feeding the separated COx and $O_2$ into a condensation system.

6. The method according to claim 1, further comprising a step in which a discharge stream containing butene remaining after the butadiene is separated in the purification apparatus is mixed with freshly supplied butene and fed into the oxidative dehydrogenation reactor.

7. The method according to claim 6, wherein the oxidative dehydrogenation reactor is operated at a reaction temperature of 150 to 650° C. under isothermal or adiabatic conditions, by using butene, oxygen ($O_2$), steam, and a gas containing n-butane remaining after the butadiene is separated in the purification apparatus as reaction raw materials, and a ferrite catalyst as a catalyst.

8. The method according to claim 1, wherein the cooling separator is operated by a quenching-type direct cooling system (quencher) or an indirect cooling system.

9. The method according to claim 1, wherein the degasification column is operated by stripping.

10. The method according to claim 1, wherein heat generated when COx and $O_2$ separated in the condenser are incinerated is used to heat the raw materials or reused in the purification apparatus.

* * * * *